United States Patent [19]

Bente, III et al.

[11] Patent Number: 4,810,456
[45] Date of Patent: Mar. 7, 1989

[54] METHOD OF PREVENTING SHRINKAGE DEFECTS IN ELECTROPHORETIC GEL COLUMNS

[75] Inventors: Paul F. Bente, III, Half Moon Bay; Joel Myerson, Berkeley, both of Calif.

[73] Assignee: Hewlett-Packard Company, Palo Alto, Calif.

[21] Appl. No.: 946,568

[22] Filed: Dec. 24, 1986

[51] Int. Cl.$^4$ .......................... B29C 43/20; B32B 1/08; C25D 13/08

[52] U.S. Cl. .................... 264/510; 204/180.1; 204/182.8; 204/299 R; 252/315.1; 264/570; 264/135; 264/267; 264/319; 264/311.19

[58] Field of Search ............... 264/570, 512, 552, 319, 264/41, 236, 331.18, 331.19, 347, 510, 265, 267, 135; 204/182.8, 299 R, 180.1, 180.2; 252/315.1

[56] References Cited

U.S. PATENT DOCUMENTS

| | | | |
|---|---|---|---|
| 2,760,233 | 8/1956 | Bjorksten | 264/512 |
| 3,216,060 | 11/1965 | Trojanowski et al. | 425/89 |
| 3,577,635 | 5/1971 | Bergman | 264/570 |
| 3,767,757 | 10/1973 | Vroom et al. | 264/570 |
| 3,803,277 | 4/1974 | Bassett | 264/48 |
| 4,230,717 | 12/1980 | Wintner | 264/108 |
| 4,415,428 | 11/1983 | Nochumson et al. | 204/299 R |
| 4,496,502 | 1/1985 | Kutowy et al. | 264/41 |
| 4,600,641 | 7/1986 | Ogawa et al. | 428/355 |

Primary Examiner—Jan H. Silbaugh
Assistant Examiner—Mary Lynn Fertig

[57] ABSTRACT

In forming an electrophoretic gel, various defects can be induced by the shrinkage that generally accompanies polymerization. These defects can include pulling away from a vessel wall or voids or bubbles forming within the gel itself. Prior to polymerization, a monomer can be compressed to a density at least equal to that of the expected density of the final gel, which then is substantially free of such shrinkage defects. The disclosed method is readily generalizable to other situations to produce polymers substantially free of defects due to shrinkage.

20 Claims, 1 Drawing Sheet

METHOD OF PREVENTING SHRINKAGE DEFECTS IN ELECTROPHORETIC GEL COLUMNS

BACKGROUND OF THE INVENTION

The present invention relates to polymer chemistry, and, more particularly, to a method of minimizing defects due to shrinkage during polymerization.

While not so limited in scope, the present invention arose in the context of polyacrylamide gel electrophoresis, in which columns of gels are prepared in tubes. During electrophoresis, an ionic sample is located at one end of the column. The ionized components migrate differentially according to charge and bulk under the influence of an axially applied electric field. After a predetermined time, the electric field is removed and the components analyzed according to axial position along the tube.

The columns of gel can be prepared by filling a tube with an aqueous mixture of acrylamide monomer, and then polymerizing the monomer. In the case of acrylamide, as is generally true in polymer chemistry, the polymer is substantially denser than the original prepolymer, e.g., the monomer, dimer, or oligomer, from which the polymer is formed. Accordingly, significant shrinkage occurs during polymerization.

As a consequence of this shrinkage, the forming gel has a tendency to pull away from the interior walls of the tube. The voids thus formed between the tube and the gel can disturb the uniformity of an applied electrio field, and seriously diminish the resolution of the electrophoresis process Furthermore, the separation of the gel from the tube aggravates a tendency of the gel to migrate out of the tube during electrophoresis.

These problem can be addressed by coating the interior of the tube with a bonding agent which forms covalent bonds between the surface of the tube and the polymer chains While separation and resulting migration are mitigated, the tension introduced by tendency to shrink during polymerization can cause bubble-like voids within the gel itself. These internal voids also distort an applied electrio field and diminish the resolution of the electrophoresis process.

The voids due to shrinkage are not amenable to procedures used to minimize bubbles formed from dissolved gasses. The latter can be minimized by degassing the prepolymer or by conducting polymerization under moderate pressure of one hundred and some odd pounds per square inch (psi). While effective at preventing bubbles formed from dissolved gasses, these methods have negligible impact on voids induced by shrinkage.

The problem of shrinkage-induced voids is not limited to electrophoresis gels. Polymerization is generally accompanied by increases in density, viscosity, and, particularly in the cases of cross-linked polymers, rigidity. Where the polymerizing substance is constrained in some way, e.g., by vessel walls and/or a bonding agent, it can occur that the polymerizing substance cannot respond to continuing increases in density in a fluid or elastic manner. In such cases, the forming polymer structure can rupture haphazardly. This is problematic where it is desired to precisely control the dimensions and uniformity of the resulting polymer.

Thus, what is needed generally is a method of preventing defects induced by shrinkage during polymerization. Specifically, it is desired to reliably produce columns of polyacrylamide gel without voids internal to the gel or between the gel and the interior wall of the confining vessel, or shrinkage of the gel along the axis of the column.

SUMMARY OF THE INVENTION

Defects due to shrinkage during polymerization can be minimized by decreasing or eliminating the shrinkage itself by compressing the prepolymer and maintaining increased density during polymerization In one realization of the present invention, the density of the polymer product is achieved in the prepolymer form and during polymerization; thus shrinkage, along wih any defects induced thereby, is eliminated. However, this is a special case within an empirically determinable range of options that result in substantially shrinkage-defect-free polymers.

In a reduction to practice of the present invention, an aqueous solution of 10% by weight acrylamide monomer was introduced into a meter long capillary tube, previously treated with a bonding agent. The tube was placed in a pressurizing chamber, which then pressurized to 10,000 psi until polymerization was completed. The result was a substantially defect-free electrophoresis gel.

This example illustrates four boundary conditions on the range of time-functions of compression covered by the present invention. (1) the pressures applied in the prior art to minimize bubbles from dissolved gasses are negligible compared to the pressures required by the present invention to minimize shrinkage defects; (2) the compression can exceed that needed to achieve the density of the polymer product; (3) the compression need not be constant; and (4) it is not necessary to eliminate all tendency to shrink to substantially eliminate the defects. This fourth point leads to a fifth: (5) the compression can be less than that needed to achieve the density of the polymer product.

With respect to the first point above, the 10,000 psi pressure is two orders of magnitude greater than that used to eliminate bubbles caused by dissolved gasses. While 10,000 psi is by no means the minimum pressure prescribed by the present invention in all situations, this magnitude helps explain the inability of pressures selected to minimize gaseous discharge to impact shrinkage defects. The issue of pressure magnitudes is addressed more precisely once the remaining of the previous paragraph's five points are elaborated.

Regarding the second point, it was calculated that the density increase during polymerization in the absence of compression would be about 2.2% and, accordingly, a pressure of about 8200 psi applied to the monomer mixture would suffice to achieve the desired pre-compression. It would be difficult to conjecture how, if a certain high pressure were effective at preventing shrinkage, an even higher pressure would cause such defects to reappear. The experiment suggests that, in fact, shrinkage defects do not reappear at higher pressures. Thus, upper limits on applicable pressures are to be imposed by costs and equipment limitations rather than by the principle of the present invention.

Turning to the third point, to the extent that an applied pressure is effectively constant, the density of the substance increases with polymerization. To illustrate, assume that the constant pressure applied is that required to achieve a density in the monomer mixture equal to the density of the polymer product in the absence of compression. However, upon completion of polymerization, the polymer product is under the constant pressure, and is thus compressed relative to its uncompressed state and thus is compressed relative to the compressed monomer mixture. This illustrates that both constant pressure and constant compression, and a wide range of alternative time-functions of compression are provided for by the present invention.

This leads into the fourth point that it is not necessary to eliminate all shrinkage. In other words, some shrinkage can be accommodated without causing defects. However, as is well known, the ratio of compression to pressure generally decreases with density so that compression of the monomer mixture is greater than compression of the polymer product, and thus the shrinkage is less with greater pressure.

The fifth point is that since some shrinkage is tolerable, it is not necessary that the initial compression completely achieve the density of the uncompressed polymer product. In some cases, the fluidity or elasticity of the polymerizing substance or the polymer product can accommodate the increase in density without inducing defects. Alternatively, the structural strength of the polymer product can be great enough to withstand the negative pressure induced by the tendency to shrink; accordingly such a polymer can maintain itself in a meta-stable state.

In practice, an applied constant pressure is not necessarily constant in effect. As applied to the reduction to practice described above, the increase in viscosity at the ends of the tube during polymerization serves to partially isolate the substance in the more central portions of the tube from the effects of the applied pressure. Thus, even where the externally applied pressure is constant, the effective internal pressure may not be. This phenomenon and its implications are elaborated in the detail description below. Briefly, while qualifying the understanding of the reduction to practice described above, the qualifications are readily aooommodated by the present invention.

Returning to the issue of the appropriate range of compressions or pressures to be applied to the monomer or other prepolymer substance, the minimum must normally be established empirically. Furthermore, the creation of defects is a stochastic event, so that one must establish acceptable "yields" to define a precise minimum. Notwithstanding the above, there are certain general limitations to how small a compression, and hence pressure, can be applied in accordance with the present invention.

The present invention only addresses reactions in which shrinkage defects can occur when polymerization is conducted at constant ambient pressure. This would exclude, by way of example, very dilute aqueous mixtures for two reasons. In the first place, the shrinkage of the mixture during polymerization would be fluid, so that shrinkage would be accommodated by flow rather than defect formation. In the second place, even if the polymer product were not free-flowing, the shrinkage would be small enough to be accommodated by limited fluidity, elasticity and structural strength in the polymer product Thus, the present invention is constrained to "defect prone" processes during which sufficient shrinkage could occur and which result in a sufficiently rigid polymer product for defects to be induced.

Given a "defect-prone" process, sufficient compression is required to make a significant difference statistically. While this is in part a function of the particular application, it is safe to say that the compression should at least reduce shrinkage by half to substantially prevent shrinkage defects that would otherwise occur.

Using acrylamides for example, a 1% aqueous mixture would not result in a polymer product rigid enough for shrinkage defects to occur. Furthermore, the about 0.2% shrinkage that would occur during polymerization under ambient pressure could easily be accomodated without unduly stressing even a more rigid polymer product. Yet, to reduce compression by one half would require about 330 psi. What this indicates is that even tripling the pressures applied to prevent gas discharge bubbles would not amount to practicing the present invention.

In accordance with the foregoing, the present invention can be applied to provide polymers substantially free of defects induced by shrinkage during polymerization. Specifically, the substance does not pull away from vessel walls or form voids during polymerization. Moreover, shrinkage along any axis can be prevented or minimized for reasons other than for eliminating voids.

The invention is applicable to any composition of pre-polymer, cross-linker, catalyst, initiator, and/or accelerator. A solvent or buffer system can be used, and the product can be a gel or other at least minimally rigid polymer. The polymer can be cast in any shape vessel, including a tube of any length and diameter. Since compression can be effected by immersion, the vessel can be quite fragile. The polymer can be formed unbonded or covalently bonded to an interior wall of the vessel so that the polymer does not migrate or otherwise move. Other features and advantage are apparent in the context of the detailed description below in conneotion with the following figures.

DESCRIPTION OF THE PREFERRED EMBODIMENTS

Figure 1:
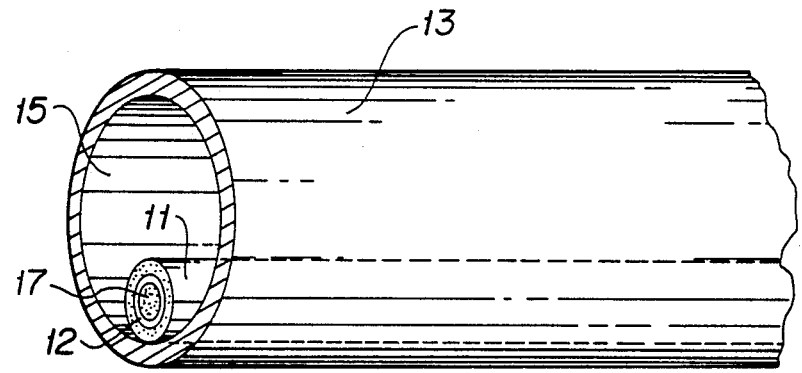
FIG. 1 is a perspective cutaway view of a pressure vessel containing a capillary tube confining a polymerizing substance in accordance with the present invention.
Figure 2:
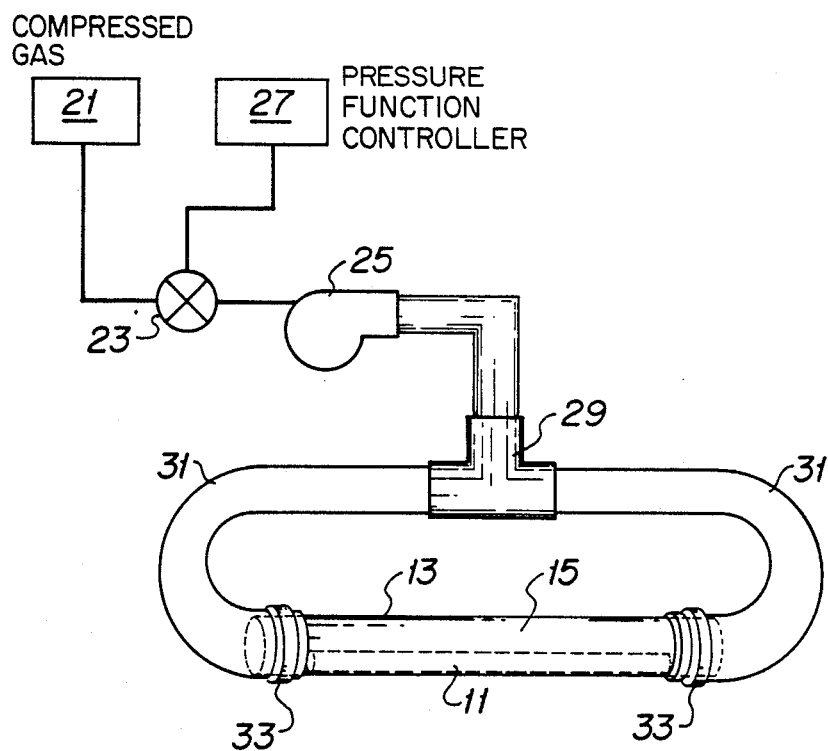
FIG. 2 is a schematic representation of a pressurizing system incorporating the pressure vessel of FIG. 1.

In accordance with the present invention, a polymerizable substance is compressed prior to polymerization to substantially avoid defects due to shrinkage during polymerization. The compression can be effected by applying pressure to the polymerizable substance.

In one embodiment of the present invention, a one meter length of fused silica capillary tube 11 is treated with a wall-bonding agent 12, such as 3-methacryloxypropyltrimethoxysilane. An aqueous mixture 17 including 10% by weight acrylamide monomer and bisacrylamide cross-linker is then introduced into the treated capillary tube 11. This filled tube 11 is inserted into a pressure chamber 13, previously filled with water 15. Sufficient ammonium persulfate initiator and tetramethylethyenediamine promoter are included in the mixture 17 to facilitate polymerization.

The pressure chamber 13 is attached to a pumping system 19 including a compressed air, or other gas, cylinder 21, a regulator valve 23, and a hydraulic amplification pump 25. As is well known, generally, the polymerization process is accompanied by shrinkage so that there is a positive density differential between the resultant polymer and the prepolymer.

A "T" connector 29 splits the pump 25 output between two delivery arms 31 so that pressure can be applied to both ends of the stainless steel cylindrical pressure chamber 13. The delivery arms 31 are sealed to the ends of the chamber 13 by means of swage-lock fittings 33.

The pumping system 19 is arranged to provide pressures sufficient to compress the prepolymer so that this differential is at least halved. Preferably, the pumping system 19 should be able to compress the prepolymer to densities beyond that of the resultant polymer.

While the monomer mixture remains in a free-flowing form, the pumping system 19 is activated to apply pressure to the polymerizable substance to increase its density beyond the expected density of the gel to be formed. In the present case, a typical cross-linked acrylamide gel (10%) by weight in water increases in density about 2.2% during the process of polymerization. Thus, pressure to be applied is selected to increase the density of the prepolymer 2.2% or more.

In order to effect this density change, a pressure of at least about 8200 psi can be applied. In the present method, a static pressure of 10,000 psi was established. Satisfactory results can usually be achieved with at least 3700 psi applied, but the probability of defects diminishes with increasing pressures. In an embodiment using a 5% monomer mixture, full compression is achieved at about 3700 psi, and 1700 psi suffices to diminish shrinkage by one half.

In the illustrated embodiment, the applied pressure is essentially maintained throughout the polymerization process. After about an hour, the polymerization process is complete. After depressurizing the chamber, the residual pressure in the gel is allowed to equilibrate with the atmosphere for about 12 hours.

The capillary tube is then removed from the pressure chamber. Except at its ends, the tube 11 now contains a uniform, polyacrylamide gel, which is substantially free of voids. The few centimeters at each end of the tube where the pressurizing water mixes with the aqueous solution are filled with unpolymerized material. If desired, the ends can be removed to provide a uniform gel. The gel is bonded to the internal wall of the tube 11.

While the illustrated embodiment used 10% by weight of monomer, 5% to 20% monomer is a suitable range. Other applications of the present invention can involve concentrations in excess of pb 20%. In iso-electric focusing applications, concentrations as low as 1% monomer can be used. However, below about 1% the change in density due to polymerization would not tend to induce srinkage defects, and so such dilute substances are not addressed by the present invention.

Pressure can be applied in various ways to the polymerizable substance, and this can effect the time function of pressure applied during polymerization. In the illustrated embodiment, pressure is applied by immersion in a bath which maintains constant pressure throughout polymerization. Thus, when polymerization is completed the pressure is reflected in internal pressure in the polymer. This internal pressure is gradually relieved after the pressur is removed.

However, pressure system 19 is equipped with a programmable pressure function controller 27 which controls the valve 23. Thus, the pressure can be adjusted during polymerization to effect constant compression or other time functions of pressure. Alternatively, constant compression can be applied using pistons at both ends of a tube containing a polymerizable substance. The pistons can be forced a fixed distance inward to achieve the desired compression. As polymerization progresses, the fixed distance remains unchanged so that pressure is gradually relieved during polymerization.

In one approach, the fixed distance is selected to establish in the prepolymer the expected density of the polymer product in the absence of compression. Thus, upon completion of polymerization, the polymer product is at atmospheric pressure and substantially free of defects due to shrinkage.

The pressure function controller 27 can be programmed to execute a wide variety of time functions of pressure provided for by the present invention to yield shrinkage-defect-free polymers. The range of pressure functions is, itself, a function of the polymers and prepolymers involved and the concentrations of these components in the substances carrying them. Also, the nature and presence of cross-linkers, initiators, and promoters, can affect the relationship between pressure and compression during polymerization. The resulting polymer can be free of negative pressure or can be meta-stable within limits of the polymer's structural strength.

As indicated above, in practice, constant external pressure is not always equated with constant internal pressure. By way of explanation, and not of limitation, the following, more detailed view of the polymerization process is presented.

During polymerization, monomers join together, increasing the viscosity of solution. If the monomer solution contains a cross-linking agent, a cross-linked network is formed. At some point during the polymerization, i.e., the gelation point, this network becomes extended and rigid enough to resist flow, and a gel results.

This gel includes water essentially trapped in the network of polymer strands. The possibility of bulk flow of water through the matrix is greatly reduced, while the tendency for small molecules to diffuse is relatively unchanged. Shrinkage results from the fact that the volume oocupied by a polymer strand is less than the sum of the volumes occupied by its constituent monomers prior to polymerization.

Among the approaches to polymerization under pressure provided for by the present invention are: constant volume or compression, constant pressure, and constant external pressure yielding constant volume. In the constant volume, the monomer solution can be compressed to the anticipated uncompressed volume of the resulting gel. The vessel bearing the monomer solution can then be sealed. This is equivalent to compressin the liquid in a cylinder with a piston and then locking the piston.

As polymerization progresses, the pressure inside decreases, while the density remains constant. At the end of polymerization, the gel is at atmospheric pressure, both internally and externally. In the piston and cylinder implementation, the piston would not moved up or down if unlocked at this point.

In the constant pressure approach, the monomer solution is compressed using a constant pressure. Sufficient pressure can be applied so that the density of the monomer solution is substantially that of the anticipated unpressurized polymer product. This can be implemented by placing a large weight on a piston capping a cylinder which holds the monomer solution.

After polymerization is completed, and after extended equilibration, the gel is under an internal pressure equal to the applied constant external pressure. When the external pressure is removed, the water that has been compressed slowly expands and flows out of the gel. The polymer network substantially maintains its shape and size. After extended re-equilibration with the atmosphere, the gel is at atmospheric pressure internally.

The constant external pressure yielding constant volume approach most closely characterizes the preferred method applied to aqueous monomer mixture 17. Although a constant pressure is applied, the polymerization is fast enough so that, at some point before completion of the polymerization process, the forming gel resists the flow of water. The ends of the gel column act as caps, or locked pistons and keep the rest of the gel substantially at constant volume.

As the polymerization proceeds, the pressure in the middle of the gel diminishes. At the completion of polymerization, the ends of the gel are under the applied pressure, while the middle is about at atmospheric pressure. Thus, the ends are effectively at constant pressure, while the center is effectively at constant volume, and intermediate reqions are effectively at intermediate pressures. If the external pressure is maintained after polymerization, the gel slowly approaches a constant pressure condition.

Applying a constant pressure greater than that required to achieve a monomer solution density equal to the density of the normally formed polymer product can yield a polymer network of greater than normal density because the polymer itself is compressed. This compressed polymer can have a tendency to expand when the pressure is released, even after water in the gel has escaped and equilibrated with the ambient atmospheric pressure. However, a cross-linked polymer can retain its compressed form along with some internal expansion tension.

If, on the other hand, the applied pressure is less than that needed to achieve a monomer solution density equal to the normal density of the polymer product, and if no shrinkage or voids are formed, the polymer network remains with some internal contraction tension.

While most of the foregoing has addressed polymer solutions and mixtures, the invention can be applied to a solvent-free polymer system. In this oase, a gel does not form and water cannot flow in and out of the network. However, the present invention can still be applied to reduce shrinkage and minimize void formation.

In addition to the foregoing variations, it is recognized that the nature of the constraints imposed on the polymerizing substance is a factor in determining appropriate pressure functions. For example, the shape of the vessel, and the nature of any bonding agents must be considered. Those skilled in the art can recognize other variations and modifications of the foregoing embodiments that are within the scope of the present invention, which is, accordingly, limited only by the following claims.

What is claimed is:

1. A method of fabricating an electrophoretic gel column including a gel substantially free of the shrinkage defects that would normally occur were the polymerization conducted at ambient pressure, said method comprising the steps of:

filling a tube with a prepolymer-bearing substance which will form a gel upon polymerization;

compressing said prepolymer-bearing substance to a density within a predetermined density range, said compression involving application of a pressure of at least about 1700 psi to said prepolymer-bearing substance; and maintaining the density of the polymerizing substance within said predetermined density range during polymerization, said density range being selected to yield a gel column substantially free of defects during shrinkage.

2. The method of claim 1 wherein said compressing step includes compressing said prepolymer-bearing substance so that the magnitude of the difference between the densities of the substance before and after compression is at least as great as the magnitude of the difference between the density of the compressed prepolymer-bearing substance and said gel in the absence of compression.

3. The methd of claim 1 wherein said compressing step includes compressing said prepolyme-bearing substance to a density at least about that of said gel in the absence of compression.

4. The method of claim 3 wherein said compressing step includes compressing said prepolymer-bearing substance to a density substantially that of said gel in the absence of compression.

5. The method of claim 1 further comprising a step of, prior to the step of filling said tube with said prepolymer-bearing substance, coating an interior wall of said tube with a bonding agent so that after polymerization said gel is bonded to said interior wall.

6. The method of claim 1 wherein said compressing step includes immersing said tube in an ambient fluid and placing said ambient fluid under pressure.

7. The method of claim 1 wherein said tube is a capillary tube.

8. The method of claim 1 wherein said step of maintaining density includes maintaining said polymerizing substance under substantially constant pressure.

9. The method of claim 1 wherein said step of maintaining density includes maintaining said polymerizing substance under substantially constant compression.

10. A method of making an electrophoretic gel column substantially free of defects due to shrinkage during polymerization, said method comprising the steps of:

filling a tube with a monomer solution which will form a gel upon polymerization said monomer constituting at least 1% by weight of said monomer solution;

compressing said monomer solution to a density within a predetermined density range, said compression involving application of a pressure of at least about 1700 psi to said monomer solution; and maintaining the density of the polymerizing solution within said predetermined density range, said predetermined density range being selected to that the resultant polymer gel is substantially free of defects due to shrinkage.

11. The method of claim 10 wherein said step of compressing includes compressing said monomer solution so that the magnitude of the difference between the densities of the compressed and uncompressed monomer solution is at least as great as the magnitude of the difference between the densities of the compressed monomer solution and the polymer gel at ambient pressure.

12. The method of claim 10 wherein said step of compressing includes compressing said monomer solution to at least the density of said polymer gel.

13. The method of claim 10 wherein said maintaining step includes maintaining the polymerizing solution at substantially constant pressure.

14. The method of claim 10 wherein said maintaining step includes maintaining the polymerizing solution at substantially constant compression.

15. The method of claim 10 further comprising a step of immersing said tube in a fluid-filled chamber prior to said compressing step.

16. The method of claim 15 wherein said compression step includes pressurizing said fluid in said chamber.

17. The method of claim 10 further comprising a step of coating an interior wall of said tube with a bonding agent before said step of filling said tube with monomer solution.

18. The method of claim 10 wherein said monomer solution includes acrylamide and bis-acrylamide.

19. The method of claim 10 wherein said compression step involves applying a pressure of at least 3700 psi to said monomer solution.

20. The method of claim 10 wherein said compression step involves applying a pressure of at least 8200 psi to said monomer solution.

* * * * *

UNITED STATES PATENT AND TRADEMARK OFFICE
CERTIFICATE OF CORRECTION

PATENT NO.    : 4,810,456
DATED         : March 7, 1989
INVENTOR(S)   : Paul E Bente, III and Joel Myerson Page 1 of 2

It is certified that error appears in the above-identified patent and that said Letters Patent is hereby corrected as shown below:

Column 1, Line 31, "electrio" should read --- electric ---;

Column 1, Line 39, "chains" should read --- chains. ---;

Column 1, Line 43, "electrio" should read --- electric ---;

Column 2, Line 10, "polymerization" should read --- polymerization. ---;

Column 3, Line 39, "aooommodated" should read --- accommodated ---;

Column 3, Line 62, "product" should read --- product. ---;

Column 4, Lines 9-10, "accomodated" should read --- accommodated ---;

Column 4, Line 35, "conneotion" should read --- connection ---;

Column 5, Line 35, "oomplete" should read --- complete ---;

Column 5, Line 49, "pb 20%" should read --- 20% ---;

Column 5, Line 63, "pressur" should read --- pressure ---;

Column 5, Line 53, "srinkage" should read --- shrinkage ---;

Column 6, Line 44, "oooupied" should read --- occupied ---;

Column 6, Line 54, "compressin" should read --- compressing ---;

Column 7, Line 25, "reqions" should read --- regions ---;

Column 7, Line 47, "oase" should read --- case ---.

UNITED STATES PATENT AND TRADEMARK OFFICE
CERTIFICATE OF CORRECTION

PATENT NO. : 4,810,456

DATED : March 7, 1989

INVENTOR(S) : Paul E. Bente, III et al

It is certified that error appears in the above-identified patent and that said Letters Patent is hereby corrected as shown below:

Column 7, line 47, "oase" should read --- case ---.

Signed and Sealed this

Twenty-sixth Day of September, 1989

Attest:

DONALD J. QUIGG

Attesting Officer

Commissioner of Patents and Trademarks